United States Patent [19]

Dudzinski

[11] 4,237,140

[45] Dec. 2, 1980

[54] ANALGESIC MIXTURE OF NALBUPHINE AND ACETAMINOPHEN

[75] Inventor: John R. Dudzinski, East Northport, N.Y.

[73] Assignee: E. I. Du Pont de Nemours and Company, Wilmington, Del.

[21] Appl. No.: 40,281

[22] Filed: May 18, 1979

[51] Int. Cl.$^2$ .................. A61K 31/165; A61K 31/485
[52] U.S. Cl. ...................................... 424/260; 424/324
[58] Field of Search ................................ 424/260, 324

[56] References Cited

U.S. PATENT DOCUMENTS 3,393,197  7/1968  Pachter et al. ...................... 424/260

OTHER PUBLICATIONS

Merck Index, 7th Ed. (1960) p. 537.
Goodman et al., The Pharmacological Bases of Therapeutics, 5th Ed. (1975), p. 348.

*Primary Examiner*—Stanley J. Friedman

[57] ABSTRACT

A composition consisting essentially of nalbuphine and acetaminophen gives unexpectedly enhanced analgesic activity.

12 Claims, 1 Drawing Figure

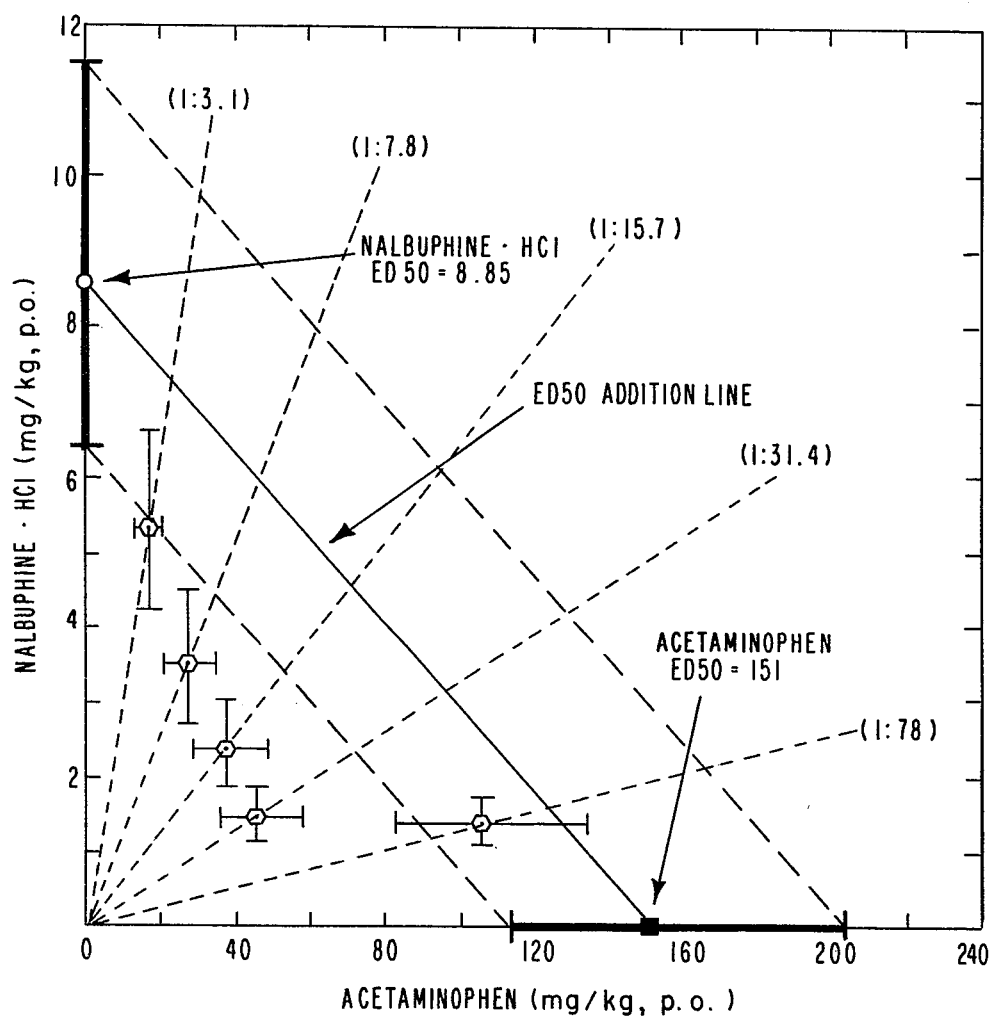

ANALGESIC MIXTURE OF NALBUPHINE AND ACETAMINOPHEN

BACKGROUND OF THE INVENTION

This invention relates to a pharmaceutical combination of compounds having analgesic activity.

U.S. Pat. No. 3,393,197 issued to Pachter and Matossian on July 16, 1968 discloses N-substituted-14-hydroxydihydronormorphines, including the N-cyclobutylmethyl derivative, commonly called nalbuphine:

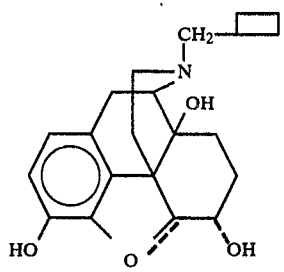

Pachter and Matossian and others, such as H. W. Elliott, et al., J. Med. (Basel), 1, 74–89 (1970); H. Blumberg, et al., Pharmacologist, 10, 189, Fall 1968; P. Roberts, Drugs of the Future, 3, 613–5 (1977), disclose the use of nalbuphine as an analgesic for the control of moderate to severe pain.

Acetaminophen, N-(4-hydroxyphenyl)acetamide, was first used in medicine by Van Mering in 1893, but only since 1949 has it gained in popularity as an effective alternative to aspirin for analgesic uses. Acetaminophen has been widely administered with a variety of other drugs, including opioid analgesics such as codeine. L. S. Goodman et al., "The Pharmacological Basis of Therapeutics," Fifth Ed., Macmillan Publishing Co., 1975, p. 348, state that it is likely that an effective dose of an opioid adds to the analgesic effect of acetaminophen as it does to that of aspirin. A. W. Pircio et al., Arch. int. Pharmacodyn., 235, 116–123 (1978), however, have reported unexpectedly enhanced analgesic action with a 1:125 mixture of butorphanol,

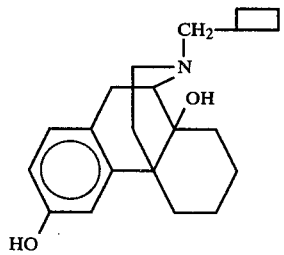

and acetaminophen; whereas a similar 1:10 combination did not show statistically-significant analgesic enhancement.

More active analgesic combinations are in constant demand because they offer the attractive possibility of relieving pain with reduced dosages thereby diminishing the expected side effects and toxicity that would result from the otherwise required higher dosages.

SUMMARY OF THE INVENTION

According to the present invention there are provided an analgesic composition consisting essentially of nalbuphine or a pharmaceutically suitable addition salt thereof and acetaminophen in a weight ratio of from about 1:2 to about 1:70, respectively, and methods of using said composition to alleviate pain in mammals.

BRIEF DESCRIPTION OF THE DRAWING

FIG. 1 is a graph showing the interaction of nalbuphine and acetaminophen on phenyl-p-benzoquinone induced writhing in mice.

DETAILED DESCRIPTION OF THE INVENTION

Nalbuphine, which has the chemical name (−)-17-(cyclobutylmethyl)-4,5α-epoxymorphinan-3,6α, 14-triol, the pharmaceutically suitable addition salts of nalbuphine, particularly the hydrochloride, and acetaminophen all have analgesic properties in man and in other mammals. In the composition of the invention nalbuphine or a pharmaceutically suitable acid addition salt thereof and acetaminophen are combined in a weight ratio of nalbuphine to acetaminophen of from about 1:2 to about 1:70, preferably, from about 1:8 to about 1:60, and most preferably from 1:15 to 1:50. It has been found that when these compounds are combined in these ranges, the resulting composition gives unexpectedly enhanced analgesic activity, i.e., the resulting activity is greater than the activity expected from the sum of the activities of the individual components. Compositions within the preferred range give the highest analgesic activity.

The composition of the invention presents the opportunity of obtaining relief from pain with reduced dosages of nalbuphine and acetaminophen, thereby diminishing the side effects and toxicity which would result from the otherwise required amounts of the individual drug components.

DOSAGE FORMS

The combination of analgesic agents of the invention can be administered to treat pain by any means that produces contact of the active agent with the agent's site of action in the body of a mammal. The composition of the invention can be administered by any conventional means available for use in conjunction with pharmaceuticals. It can be administered alone, but is generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage can be such that the active ingredient is administered at a daily dosage of from about 0.25 to 1.25 milligrams per kilogram (mg/kg) of body weight of nalbuphine and from about 10.8 to 54 mg/kg of acetaminophen. Ordinarily, administration of the composition of the invention in divided doses 2–5 times per day or in sustained release form is effective to obtain desired results.

Dosage forms (compositions) suitable for internal administration contain from about 50 milligrams to about 600 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

Suitable pharmaceutical carriers are described in *Remington's Pharmaceutical Sciences*, E. W. Martin, a standard reference text in this field.

Useful pharmaceutical dosage-forms for administration of the composition of the invention can be illustrated by the following examples:

EXAMPLE 1

| Nalbuphine/Acetaminophen Tablets (7.5/325 mg) | |
|---|---|
| Formula | mg/Tablet |
| Acetaminophen | 325.00 |
| Sucrose | 1.00 |
| Povidone | 8.00 |
| Purified Water | 10.00 |
| Modified Starch | 60.00 |
| Silica Gel | 11.00 |
| Nalbuphine . HCl | 7.50 |
| Microcrystalline Cellulose | 262.50 |
| Stearic Acid | 15.00 |
| | 700.00 mg |

A large number of tablets can be prepared by conventional procedures, utilizing the formula above.

EXAMPLE 2

| Nalbuphine/Acetaminophen Tablets (7.5/500 mg) | |
|---|---|
| Formula | mg/Tablet |
| Acetaminophen | 500.00 |
| Sucrose | 2.00 |
| Povidone | 13.00 |
| Purified Water | 15.00 |
| Modified Starch | 45.00 |
| Silica Gel | 17.00 |
| Nalbuphine . HCl | 7.50 |
| Microcrystalline Cellulose | 158.50 |
| Stearic Acid | 12.00 |
| | 770.00 mg |

A large number of tablets can be prepared by conventional procedures, utilizing the formula above.

EXAMPLE 3

| Nalbuphine/Acetaminophen Tablets | |
|---|---|
| (a) Formula (1:16) (20/325 mg/Tablet) | |
| | mg/Tablet |
| Acetaminophen | 325.00 |
| Sucrose | 1.00 |
| Povidone | 8.00 |
| Purified Water | 10.00 |
| Modified Starch | 60.00 |
| Silica Gel | 11.00 |
| Nalbuphine . HCl | 20.00 |
| Microcrystalline Cellulose | 250.00 |
| Stearic Acid | 15.00 |
| | 700.00 mg |
| (b) Formula (1:8) (40/325 mg/Tablet) | |
| | mg/Tablet |
| Acetaminophen | 325.00 |
| Sucrose | 1.00 |
| Povidone | 8.00 |
| Purified Water | 10.00 |
| Modified Starch | 60.00 |
| Silica Gel | 11.00 |
| Nalbuphine . HCl | 40.00 |
| Microcrystalline Cellulose | 230.00 |
| Stearic Acid | 15.00 |
| | 700.00 mg |

A large number of tablets can be prepared by conventional procedures, utilizing the formula above.

EXAMPLE 4

| Nalbuphine/Acetaminophen Oral Liquid | |
|---|---|
| (a) Formula (1:43) 7 ½ /325mg/10ml | |
| | Amount/10 ml |
| Acetaminophen | 325.00 mg |
| Nalbuphine . HCl | 7.50 mg |
| Propylene Glycol | 2.00 ml |
| Glycerin | 3.00 ml |
| Ethanol | 0.85 ml |
| Sorbitol Solution | 3.00 ml |
| Sodium Benzoate | 10.00 mg |
| Flavor | 0.01 ml |
| Purified Water | 10.00 ml |
| (b) Formula (1:16) 20/325 mg/10ml | |
| | Amount/10 ml |
| Acetaminophen | 325.00 mg |
| Nalbuphine . HCl | 20.00 mg |
| Propylene Glycol | 2.00 ml |
| Glycerin | 3.00 ml |
| Ethanol | 0.85 ml |
| Sorbitol Solution | 3.00 ml |
| Sodium Benzoate | 10.00 mg |
| Flavor | 0.01 ml |
| Purified Water | 10.00 ml |
| (c) Formula (1:8) 40/325mg/10ml) | |
| | Amount/10 ml |
| Acetaminophen | 325.00 mg |
| Nalbuphine . HCl | 40.00 mg |
| Propylene Glycol | 2.00 ml |
| Glycerin | 3.00 ml |
| Ethanol | 0.85 ml |
| Sorbitol Solution | 3.00 ml |
| Sodium Benzoate | 10.00 mg |
| Flavor | 0.01 ml |
| Purified Water | 10.00 ml |

An oral liquid can be prepared by conventional methods, utilizing the formulas above.

EXAMPLE 5

Nalbuphine/Acetaminophen Capsules

(a) Formula (1:43) 7½/325mg/CAP

| | mg/CAP |
|---|---|
| Acetaminophen | 325.00 |
| Nalbuphine . HCl | 7.50 |
| Modified Starch | 95.90 |
| Silicon Dioxide | 0.60 |
| Starch | 6.00 |
| | 435.00 |

(b) Formula (1:16) 20/325mg/CAP

| | mg/CAP |
|---|---|
| Acetaminophen | 325.00 |
| Nalbuphine . HCl | 20.00 |
| Modified Starch | 83.40 |
| Silicon Dioxide | 0.60 |
| Starch | 6.00 |
| | 435.00 |

(c) Formula (1:8) 40/325mg/CAP

| | mg/CAP |
|---|---|
| Acetaminophen | 325.00 |
| Nalbuphine . HCl | 40.00 |
| Modified Starch | 63.40 |
| Silicon Dioxide | 0.60 |
| Starch | 6.00 |
| | 435.00 |

A large number of unit capsules can be prepared by filling standard two-piece hard gelatin capsules with the above formulas utilizing conventional techniques.

UTILITY

Test Methods

The unexpectedly enhanced analgesic activity of the composition of the invention is evidenced by test conducted on mice. Male CF₁ mice obtained from Charles River Breeding Laboratories, fasted for 16-22 hours, and weighing 18-22 g at the time of testing are used throughout. All mice are dosed orally with acetaminophen and/or nalbuphine (calculated as the hydrochloride salt) dissolved completely in distilled water containing as vehicle 2% by volume of Tween 80 ®, a pharmacological dispersant manufactured by Fisher Scientific Company and containing 100% polysorbate 80. A dosing volume of 20 ml/kg is used. All doses are coded and the test is performed under a code not known to the observer.

ANALGESIC ACTIVITY IN THE MOUSE ANTIPHENYLQUINONE WRITHING TEST

A standard procedure for detecting and comparing the analgesic activity of different classes of analgesia drugs for which there is a good correlation with human efficacy is the prevention of phenyl-p-benzoquinone induced writhing in mice (H. Blumberg et al.; Proc. Soc. Exp. Biol. Med. 118, 763-766, 1965).

Mice, intubated with various doses of nalbuphine HCl, acetaminophen, combined doses of nalbuphine.HCl and acetaminophen, or vehicle, are injected intraperitoneally with a challenge dose of phenyl-p-benzoquinone. The phenyl-p-benzoquinone is prepared as a 0.1 mg/ml solution in 5% by volume of ethanol in water; the writhing dose is 1.25 mg/kg injected at the rate of 0.25 ml/20 g. For scoring purposes a "writhe" is indicated by whole body stretching or contraction of the abdomen: mice are observed 10 minutes for the presence or absence of writhing beginning 5 minutes after receiving the phenyl-p-benzoquinone dose. Each mouse is used only once, then discarded.

Initially the time of peak activity is determined separately for each drug in the antiphenylquinone writhing test. Then several doses of each drug alone and in precise nalbuphine.HCl/acetaminophen ratios are given orally at or near the time of peak analgesic effects.

All ED50 values are determined numerically by the moving average method of Thompson (W. F. Thompson: Bacteriological Rev. 11, 115-145, 1947) and 95% confidence limits are calculated according to the method of Litchfield and Wilcoxon (J. T. Litchfield, Jr. and F. Wilcoxon: J. Pharm. Exp. Ther. 96, 99-113, 1949). As used herein ED50 means the dosage at which 50% of the mice in a test group exhibit an analgesic response.

In a preliminary experiment, the peak time for nalbuphine.HCl analgesia was at 5 minutes, ED50=7.6 mg/kg (95% confidence limits: 5.9, 9.7). The peak time for acetaminophen analgesia was also at 5 minutes, ED50=119 mg/kg (95% confidence limits: 86, 165). Because the individual drugs both exhibited peak effects at the same time, combination doses of nalbuphine.HCl and acetaminophen (mixed together prior to a single oral dosing) were also studied for analgesic effects at 5 minutes.

The interaction of nalbuphine.HCl and acetaminophen on phenyl-p-benzoquinone induced writhing in mice and is demonstrated by the data in Table 1 and in the Loewe isobologram (S. Loewe: Pharm. Rev. 9: 237-242, 1957) in FIG. 1. In this figure, the diagonal line joining the ED50 values of the two drugs given separately represents simple additivity of drug effects. The dashed lines on each side of the diagonal line give the 95% confidence limits for this line of additivity. ED50's falling under the curve (between the line and the origin) indicate potentiation (unexpected enhancement) of effects while those outside of the curve would suggest antagonism between the two drugs. The 5 diagonal lines radiating from the origin represent the dose ratios of nalbuphine.HCl to acetaminophen used in mice receiving the combined drug dosages. The horizontal and vertical bars through each ED50 point are the 95% confidence limits. FIG. 1 shows that compositions of the invention having a ratio of nalbuphine.HCl to acetaminophen from 1:2 to 1:7 0 give unexpectedly enhanced activity since the 95% confidence limits of the ED50 values for those ratios do not overlap the line of additivity.

TABLE 1

| ORAL NALBUPHINE . HCl/ACETAMINOPHEN COMBINATIONS IN THE MOUSE ANTIPHENYLQUINONE WRITHING TEST (N = Mice/Dose) | | | | | |
|---|---|---|---|---|---|
| DRUG COMBINATIONS Nalbuphine . HCL: Acetaminophen | DRUG DOSE (mg/kg) | | % MICE BLOCKED | ED50 AT 5 MIN. (95% Confidence Limits) | |
| | Nalbuphine . HCl | Acetaminophen | | Nalbuphine . HCl | Acetaminophen |
| — | 0 | 0 | 3.3% | — | — |
| | 1.9 | 0 | 10% | | |

TABLE 1-continued

ORAL NALBUPHINE . HCl/ACETAMINOPHEN COMBINATIONS
IN THE MOUSE ANTIPHENYLQUINONE WRITHING TEST
(N = Mice/Dose)

| DRUG COMBINATIONS Nalbuphine . HCL: Acetaminophen | DRUG DOSE (mg/kg) | | % MICE BLOCKED | ED50 AT 5 MIN. (95% Confidence Limits) | |
|---|---|---|---|---|---|
| | Nalbuphine . HCl | Acetaminophen | | Nalbuphine . HCl | Acetaminophen |
| (Nalbuphine . HCl only) | 3.8 | 0 | 23% | 8.58 (6.4–11.5) | — |
| | 7.6 | 0 | 50% | | |
| | 15.2 | 0 | 63% | | |
| | 30.4 | 0 | 90% | | |
| 1:3.1 | 1.58 | 4.95 | 3.3% | 5.30 (4.46–6.59) | 16.6 (13.3–20.7) |
| | 3.17 | 9.9 | 17% | | |
| | 6.33 | 19.8 | 63% | | |
| | 12.7 | 39.6 | 93% | | |
| | 25.3 | 79.2 | 100% | | |
| 1:7.8 | 1.27 | 9.93 | 23% | 3.50 (2.7–4.5) | 27.4 (21.2–35.3) |
| | 2.54 | 19.9 | 23% | | |
| | 5.07 | 39.7 | 73% | | |
| | 10.1 | 79.4 | 90% | | |
| | 20.3 | 159. | 97% | | |
| 1:15.7 | 0.95 | 14.9 | 13% | 2.37 (1.86–3.03) | 37.2 (28.6–48.4) |
| | 1.9 | 29.8 | 40% | | |
| | 3.8 | 59.5 | 70% | | |
| | 7.6 | 119 | 97% | | |
| | 15.2 | 238 | 100% | | |
| 1:31.4 | 0.63 | 19.8 | 20% | 1.45 (1.14–1.85) | 45.4 (35.5–58.0) |
| | 1.27 | 39.7 | 55% | | |
| | 2.53 | 79.3 | 60% | | |
| | 5.1 | 159 | 97% | | |
| | 10.1 | 317 | 100% | | |
| 1:78 | 0.32 | 24.8 | 10% | 1.36 (1.08–1.72) | 106 (83.1–135) |
| | 0.64 | 49.6 | 23% | | |
| | 1.27 | 99.2 | 43% | | |
| | 2.54 | 198 | 70% | | |
| | 5.08 | 397 | 100% | | |
| (Acetaminophen only) | 0 | 29.8 | 20% | — | 151 (113–203) |
| | 0 | 59.5 | 23% | | |
| | 0 | 119 | 50% | | |
| | 0 | 238 | 55% | | |

What is claimed is:

1. A pharmaceutical composition consisting essentially of (a) nalbuphine or a pharmaceutically suitable acid addition salt thereof and (b) acetaminophen in a weight ratio of (a) to (b) of from about 1:2 to about 1:70.

2. The composition of claim 1 wherein the weight ratio is from about 1:8 to about 1:60.

3. The composition of claim 1 wherein the weight ratio is from about 1:15 to about 1:50.

4. The composition of claim 1 wherein the nalbuphine is present as the hydrochloride salt.

5. The composition of claim 1 which contains in addition a suitable pharmaceutical carrier.

6. The composition of claim 2 which contains in addition a suitable pharmaceutical carrier.

7. The composition of claim 3 which contains in addition a suitable pharmaceutical carrier.

8. The composition of claim 4 which contains in addition a suitable pharmaceutical carrier.

9. A method of alleviating pain in a mammal which comprises administering to the mammal an effective analgesic amount of the compoisition of claim 1.

10. A method of alleviating pain in a mammal which comprises administering to the mammal an effective analgesic amount of the composition of claim 2.

11. A method of alleviating pain in a mammal which comprises administering to the mammal an effective analgesic amount of the composition of claim 3.

12. A method of alleviating pain in a mammal which comprises administering to the mammal an effective analgesic amount of the composition of claim 4.

* * * * *